US011129731B2

(12) United States Patent
Miller et al.

(10) Patent No.: US 11,129,731 B2
(45) Date of Patent: *Sep. 28, 2021

(54) PIVOTING WEDGE EXPANDING SPINAL IMPLANT AND METHOD OF IMPLANTING SAME

(71) Applicant: WARSAW ORTHOPEDIC, INC., Warsaw, IN (US)

(72) Inventors: Keith E. Miller, Germantown, TN (US); Anthony J. Melkent, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/730,151

(22) Filed: Dec. 30, 2019

(65) Prior Publication Data

US 2020/0129306 A1 Apr. 30, 2020

Related U.S. Application Data

(60) Continuation of application No. 16/115,726, filed on Aug. 29, 2018, now Pat. No. 10,531,964, which is a division of application No. 14/987,519, filed on Jan. 4, 2016, now Pat. No. 10,076,423.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30405* (2013.01); *A61F 2002/30462* (2013.01); *A61F 2002/30471* (2013.01); *A61F 2002/30507* (2013.01); *A61F 2002/30515* (2013.01); *A61F 2002/30538* (2013.01);
(Continued)

(58) Field of Classification Search
CPC ...... A61F 2/4455; A61F 2/446; A61F 2/4465; A61F 2/447
See application file for complete search history.

(56) References Cited

U.S. PATENT DOCUMENTS 7,850,733 B2 12/2010 Byanham et al.
7,875,078 B2 1/2011 Wysocki et al.
7,909,869 B2 3/2011 Gordon et al.
(Continued)

FOREIGN PATENT DOCUMENTS

FR 2771282 5/1999
WO WO2017120045 7/2017

OTHER PUBLICATIONS

International Search Report and Written Opinion dated Apr. 14, 2017 in PCT/US2016/067931.

*Primary Examiner* — Julianna N Harvey (57) ABSTRACT

A pivoting wedge expandable spinal implant. An upper portion and a lower portion are pivotally connected together. The implant, in a collapsed position, is inserted into a disc space. A driving screw engages and applies a force to a pushing portion, driving the pushing portion toward the implant's distal end. The pushing portion engages and drives a wedge toward the implant's distal end. The wedge pivots upward against an inner surface of the lower portion. The wedge continues to pivot along an inner surface of the upper portion, translating the force to the upper portion, pivoting and expanding the upper portion to an expanded position.

20 Claims, 12 Drawing Sheets

(52) U.S. Cl.
CPC ............... *A61F 2002/30593* (2013.01); *A61F 2002/30904* (2013.01); *A61F 2220/0041* (2013.01)

(56) References Cited

U.S. PATENT DOCUMENTS

| | | | |
|---|---|---|---|
| 8,062,375 | B2 | 11/2011 | Glerum et al. |
| 8,105,358 | B2 | 1/2012 | Phan |
| 8,105,382 | B2 | 1/2012 | Olmos et al. |
| 8,123,810 | B2 | 2/2012 | Gordon et al. |
| 8,133,232 | B2 | 3/2012 | Levy et al. |
| 8,187,332 | B2 | 5/2012 | Mcluen |
| 8,382,842 | B2 | 2/2013 | Greenhalgh et al. |
| 8,394,145 | B2 | 3/2013 | Weiman |
| 8,398,713 | B2 | 3/2013 | Weiman |
| 8,403,990 | B2 | 3/2013 | Dryer et al. |
| 8,435,298 | B2 | 5/2013 | Weiman |
| 8,491,659 | B2 | 7/2013 | Weiman |
| 8,518,120 | B2 | 8/2013 | Glerum et al. |
| 8,523,944 | B2 | 9/2013 | Jimenez et al. |
| 8,556,979 | B2 | 10/2013 | Weiman et al. |
| 8,568,481 | B2 | 10/2013 | Olmos et al. |
| 8,628,577 | B1 | 1/2014 | Jimenez |
| 8,628,578 | B2 | 1/2014 | Miller et al. |
| 8,632,595 | B2 | 1/2014 | Weiman |
| 8,663,329 | B2 | 3/2014 | Ernst |
| 8,679,183 | B2 | 3/2014 | Glerum et al. |
| 8,685,098 | B2 | 4/2014 | Glerum et al. |
| 8,709,086 | B2 | 4/2014 | Glerum et al. |
| 8,778,025 | B2 | 7/2014 | Ragab et al. |
| 8,795,366 | B2 | 8/2014 | Varela |
| 8,888,853 | B2 | 11/2014 | Glerum et al. |
| 8,888,854 | B2 | 11/2014 | Glerum et al. |
| 8,894,711 | B2 | 11/2014 | Varela |
| 8,894,712 | B2 | 11/2014 | Varela |
| 8,926,704 | B2 | 1/2015 | Glerum |
| 8,940,049 | B1 | 1/2015 | Jimenez |
| 9,039,771 | B2 | 5/2015 | Glerum et al. |
| 9,119,730 | B2 | 9/2015 | Glerum et al. |
| 10,076,423 | B2 * | 9/2018 | Miller ............... A61F 2/447 |
| 10,531,964 | B2 | 1/2020 | Miller et al. |
| 2008/0288071 | A1 | 11/2008 | Biyani |
| 2010/0280622 | A1 | 11/2010 | McKinley |
| 2011/0054621 | A1 | 3/2011 | Lim |
| 2011/0172721 | A1 | 4/2011 | Verala |
| 2011/0172774 | A1 | 7/2011 | Varela |
| 2012/0029636 | A1 | 2/2012 | Ragab et al. |
| 2012/0035729 | A1 | 2/2012 | Glerum et al. |
| 2012/0109319 | A1 | 5/2012 | Perisic |
| 2012/0150304 | A1 | 6/2012 | Glerum et al. |
| 2012/0150305 | A1 | 6/2012 | Glerum et al. |
| 2012/0158146 | A1 | 6/2012 | Glerum et al. |
| 2012/0158147 | A1 | 6/2012 | Glerum et al. |
| 2012/0158148 | A1 | 6/2012 | Glerum et al. |
| 2012/0185049 | A1 | 7/2012 | Varela |
| 2012/0203347 | A1 | 8/2012 | Glerum |
| 2013/0144388 | A1 | 6/2013 | Emery et al. |
| 2013/0158664 | A1 * | 6/2013 | Palmatier ............... A61F 2/447 623/17.16 |
| 2014/0058512 | A1 | 2/2014 | Petersheim |
| 2014/0121774 | A1 | 5/2014 | Glerum et al. |
| 2014/0163682 | A1 | 6/2014 | Lott et al. |
| 2014/0236296 | A1 | 8/2014 | Wagner |
| 2014/0249630 | A1 | 9/2014 | Weiman |
| 2014/0277489 | A1 | 9/2014 | Davenport et al. |
| 2014/0277500 | A1 | 9/2014 | Logan |
| 2014/0324171 | A1 | 10/2014 | Glerum et al. |
| 2015/0012097 | A1 | 1/2015 | Ibarra |
| 2015/0272743 | A1 * | 10/2015 | Jimenez ............... A61F 2/447 623/17.16 |
| 2015/0374508 | A1 | 12/2015 | Sandul |
| 2016/0022438 | A1 | 1/2016 | Lamborne |
| 2016/0120660 | A1 * | 5/2016 | Melkent ............... A61F 2/4455 623/17.16 |
| 2017/0112630 | A1 * | 4/2017 | Kuyler ............... A61F 2/4455 |
| 2017/0189200 | A1 | 7/2017 | Miller et al. |
| 2018/0360615 | A1 | 12/2018 | Miller et al. |
| 2020/0129306 | A1 | 4/2020 | Miller et al. |

* cited by examiner

PIVOTING WEDGE EXPANDING SPINAL IMPLANT AND METHOD OF IMPLANTING SAME

This application is a continuation of U.S. application Ser. No. 16/115,726 filed Aug. 29, 2018; which is a divisional of U.S. application Ser. No. 14/987,519 filed Jan. 4, 2016; all of which are incorporated herein by reference.

BACKGROUND OF THE INVENTION

Field of the Invention

The present invention relates to a spinal implant. More particularly, the invention relates to an expandable spinal implant having a pivoting wedge, configured to expand within a patient's disc space between two adjacent vertebral bodies, from a collapsed position to an expanded position.

Description of the Related Art

Expandable spinal implants are known in the art. Such expandable implants can be configured to have lordotic, tapered configurations to assist in the restoration or enhancement of spinal lordosis. The expandability of such implants allows placement of the implant, while in a collapsed position, through a relatively small opening in a patient's body, into a corresponding surgically-enhanced disc space between two adjacent vertebral bodies. Thereafter, expansion of the implant within the disc space increases the height between the two adjacent vertebral bodies, assisting in the restoration or enhancement of spinal lordosis.

The related art expandable implants typically have two components, pivotally held together by a pivot pin. During expansion of the implant to the expanded position, the pin, in some cases, may be incapable of withstanding all of the forces generated between the two components, resulting in damage to, and inoperability of, the implant.

SUMMARY OF THE INVENTION

It is an object of the present invention to provide an expandable spinal implant which obviates one or more of the shortcomings of the related art.

It is another object of the present invention to provide a pivoting wedge expandable spinal implant for insertion into a patient's disc space between an upper vertebral body and a lower vertebral body. The implant has a proximal end and a distal end defining a mid-longitudinal axis. The implant is expandable between a collapsed position and an expanded position. The implant includes an upper portion. The upper portion has a proximal end and a distal end. The upper portion also has an inner surface and an outer surface. The outer surface is configured to engage a vertebral endplate of the upper vertebral body. The inner surface has an upper ramp surface.

The implant further includes a lower portion. The lower portion is pivotally engaged with the upper portion, and has a proximal end and a distal end. The proximal end includes a threaded proximal end opening. The lower portion also has an inner surface and an outer surface. The outer surface is configured to engage a vertebral endplate of the lower vertebral body. The inner surface includes a lower ramp surface. The lower ramp surface and the upper ramp surface define an internal pocket therebetween.

A force application device is configured to be inserted into the proximal end threaded opening. The force application device includes a distal end.

A pushing portion is defined in the proximal end of the implant. The pushing portion has a proximal end and a distal end. The proximal end of the pushing portion is configured to come into contact with the distal end of the force application device.

A wedge is defined in the distal end of the implant. The wedge has a proximal end and a distal end. The proximal end of the wedge is configured to be in contact with the distal end of the pushing portion. The distal end of the wedge is configured to be positioned, when the implant is in the collapsed position, within the internal pocket defined by the upper ramp surface and the lower ramp surface. The distal end of the wedge is further configured, when force is applied by the force application device to the pushing portion, forcing the pushing portion to move in the direction of the distal end of the implant, to be moved, by the pushing portion, up along the lower ramp surface and into contact with the upper ramp surface, translating the motion to the upper ramp surface, thereby and moving the upper ramp portion away from the lower ramp portion. The distal end of the wedge further moves up along the upper ramp surface, further expanding the implant until it reaches the expanded position.

It is a further object of the present invention to provide a method of inserting the expandable spinal implant as described above into a patient's disc space between an upper vertebral body and a lower vertebral body.

The method includes surgically preparing a disc space between a lower vertebral body and an upper vertebral body, inserting the implant described above, in the collapsed position, into the disc space, with the force application device applying a force to the pushing portion, thereby pushing the pushing portion toward the distal end of the implant, pushing the wedge toward the distal end of the implant, up the lower ramp surface and into contact with at least a portion of the upper ramp surface, translating the force to the upper ramp surface, moving the upper ramp portion away from the lower ramp portion, pushing the distal end of the wedge up the upper ramp surface, and expanding the implant to the expanded position.

These and other objects of the present invention will be apparent from review of the following specification and the accompanying drawings.

DETAILED DESCRIPTION OF THE PREFERRED EMBODIMENT

In accordance with the invention, and as depicted in FIGS. 1-15, a pivoting wedge expandable spinal implant 10 is provided, configured to be inserted in a surgically-enhanced disc space between an upper vertebral body and a lower vertebral body (not shown). The implant includes a proximal end 12 and a distal end 14, defining a mid-longitudinal axis L-L therebetween.

In accordance with the invention, the implant includes an upper portion 16. The upper portion 16 includes a proximal end 18, a distal end 20, an inner surface 22, and an outer surface 24.

Figure 1:
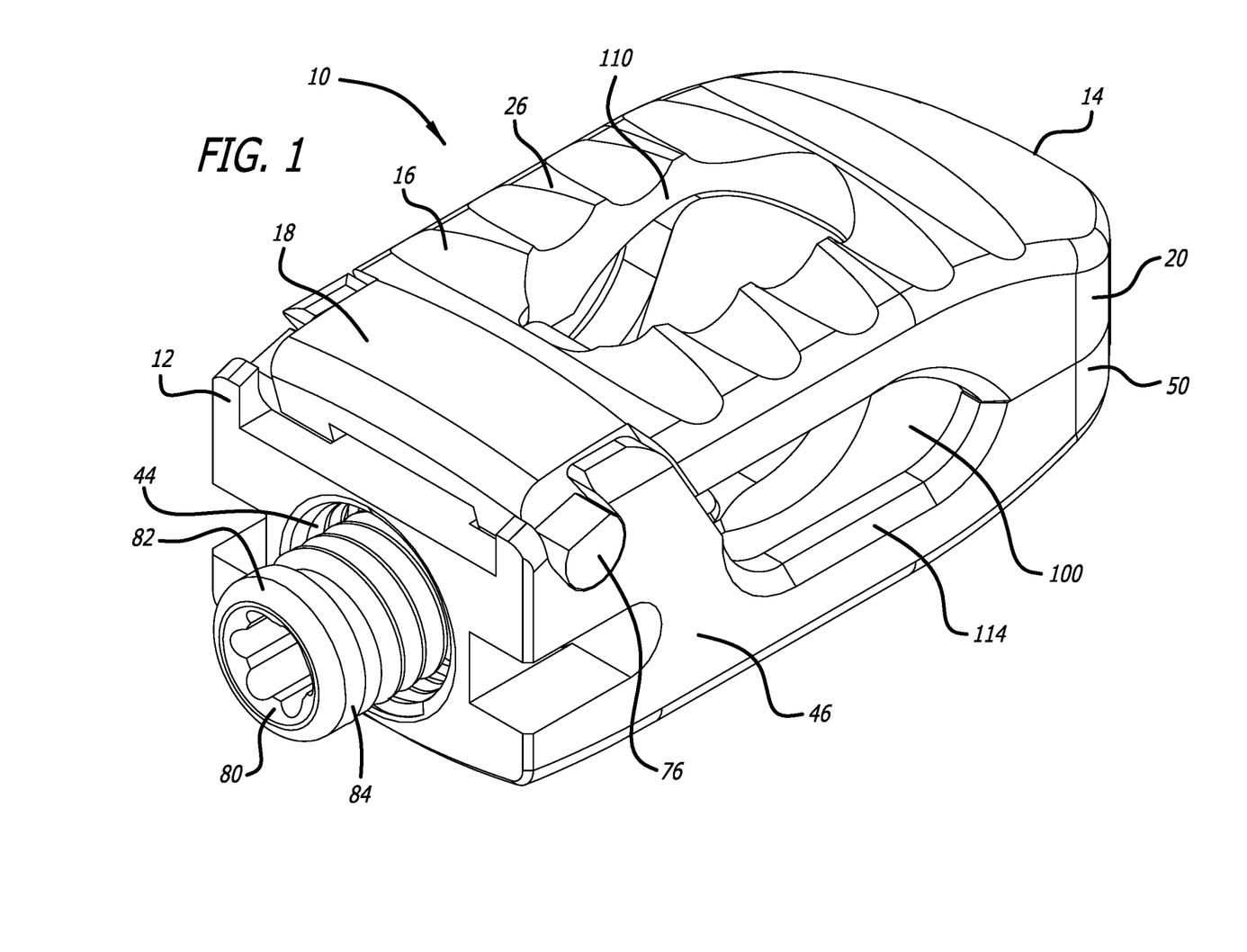
FIG. 1 is a lower perspective view of a pivoting wedge expandable spinal implant in accordance with the invention.
Figure 2:
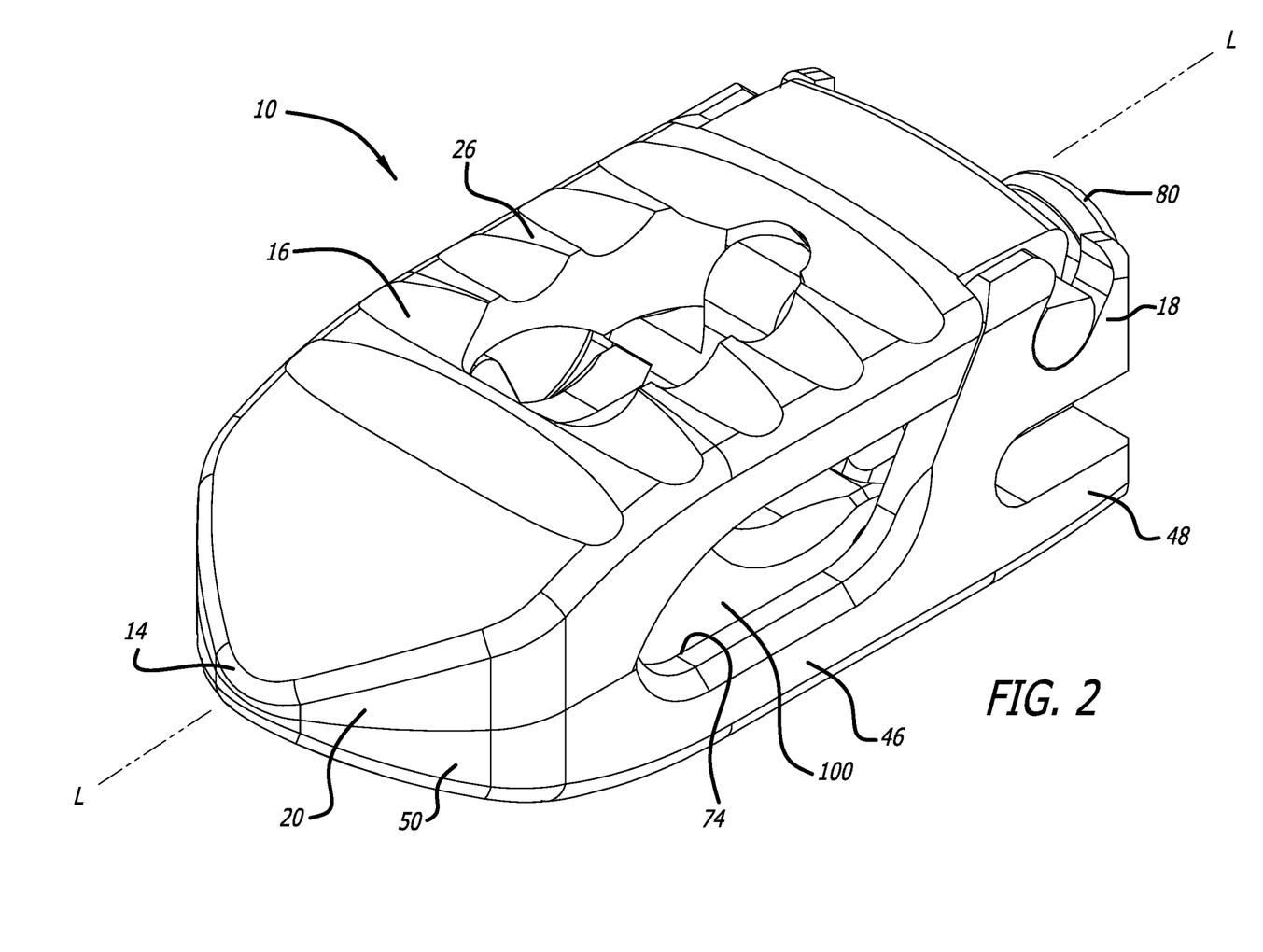
FIG. 2 is an upper perspective view of a pivoting wedge expandable spinal implant in accordance with the invention.

In accordance with the invention, and as depicted in FIG. 2, the distal end 14 is preferably tapered, for simplicity of access to the disc space.

The outer surface 24 includes one or more raised ridges 26, for engaging a vertebral endplate of the upper vertebral body.

Figures 3, 3A:
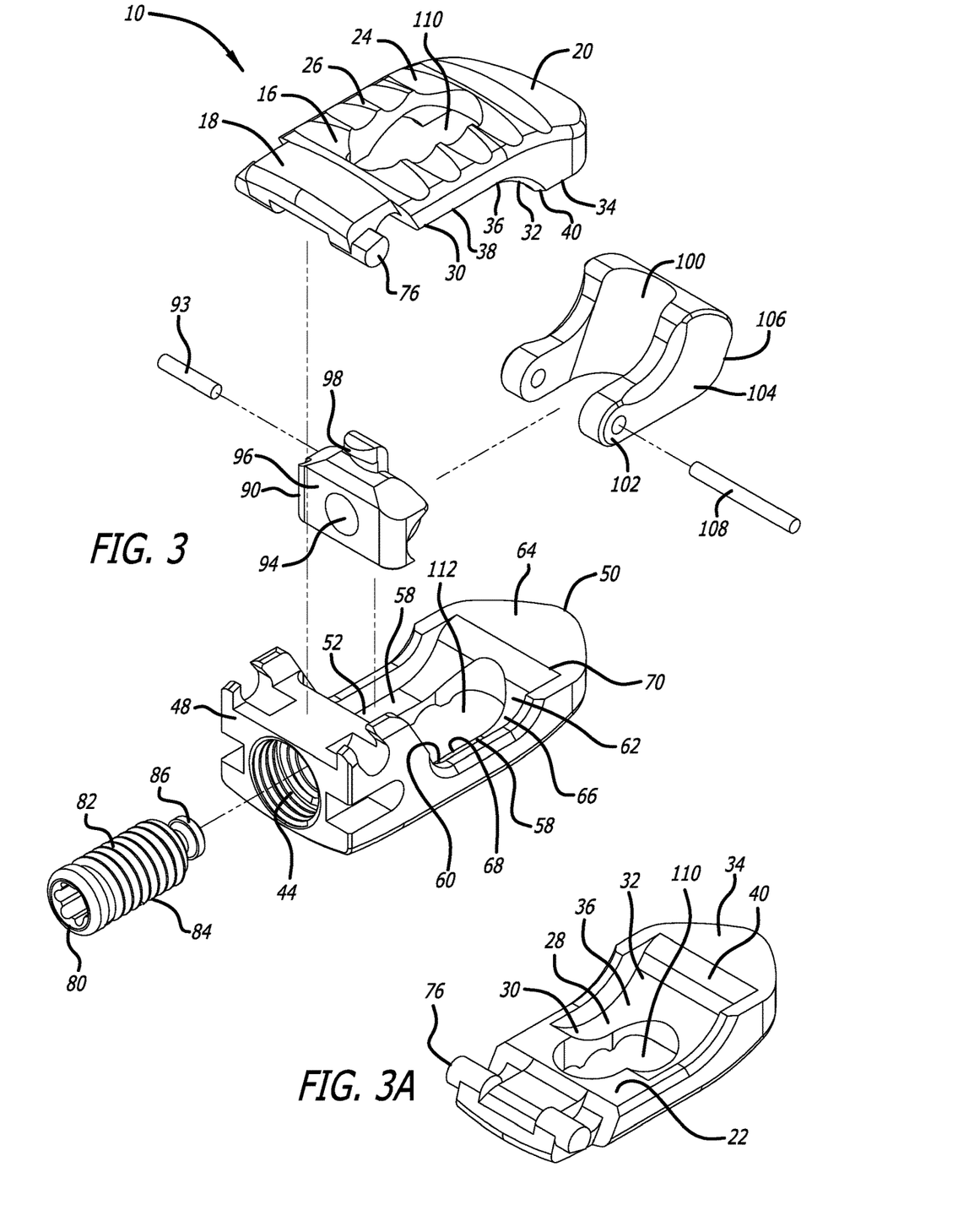
FIG. 3 is an exploded parts view of a pivoting wedge expandable spinal implant in accordance with the invention.
FIG. 3A is a perspective view of an upper portion of the pivoting wedge expandable spinal implant in accordance with the invention, flipped over to depict an interior configuration of the upper portion, including an upper ramp portion.
Figure 15:
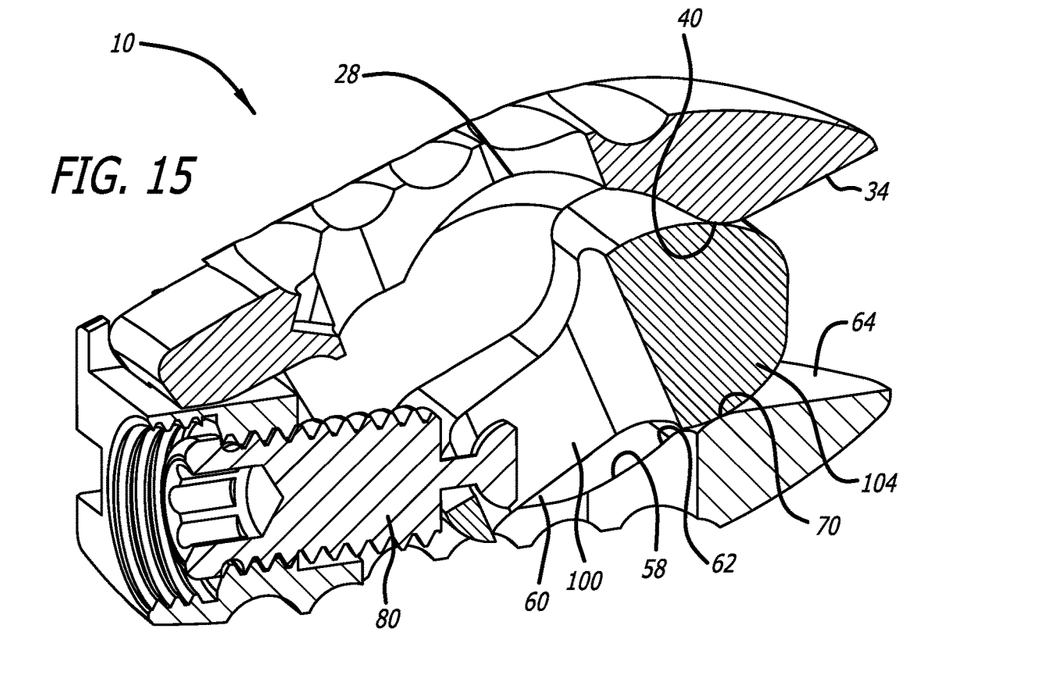
FIG. 15 is a lower perspective cross-sectional view of a pivoting wedge expandable spinal implant in accordance with the invention, without a pushing portion, and with a distal end of the force application device configured to contact a proximal end of the wedge, expanded to an 80% expanded position.
Figure 16:
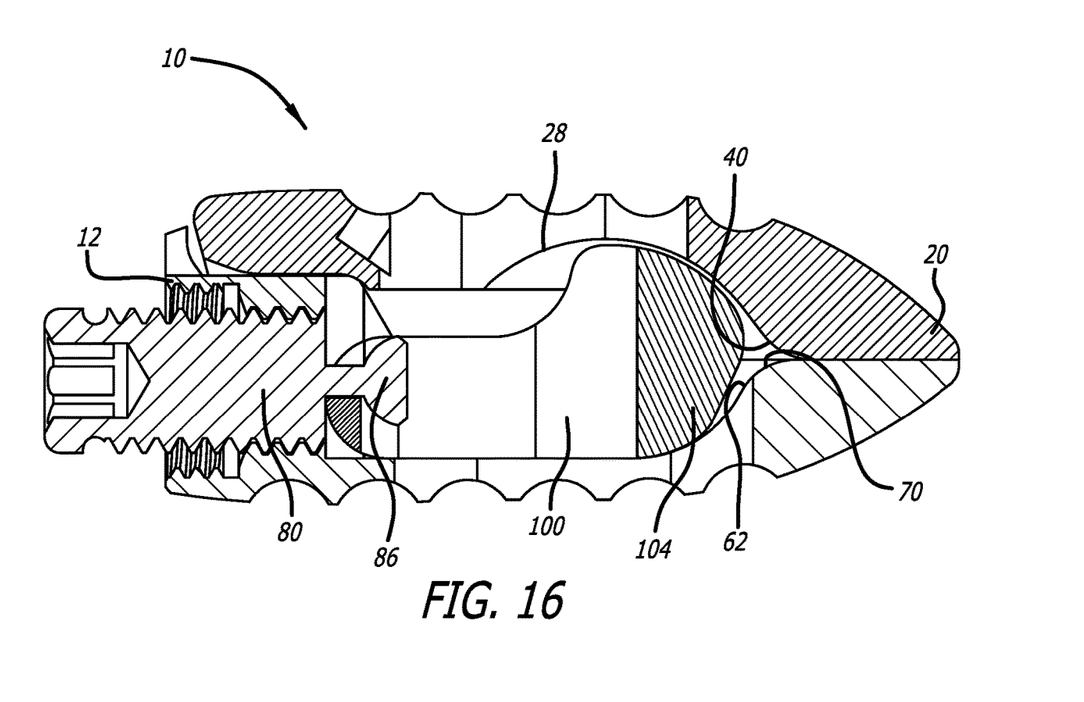
FIG. 16 is a side cross-sectional view of the pivotal wedge expandable spinal implant depicted in FIG. 15, in the collapsed position.

In accordance with the invention, and as depicted in FIGS. 3, 3A, and 15, the inner surface 22 defines an upper ramp surface 28. The upper ramp surface 28 extends from a first position 30 intermediate the proximal end 18 and the distal end 20, to a second position 32 proximate the distal end 14 of the implant 10. A first planar surface 34 extends from the second position 32 to the distal end 14 of the implant 10. The upper ramp surface 28 includes an arcuate portion 36 proximate the second position 32. The arcuate portion 36 intersects with the first planar surface 34 at a first transition point 40. The invention is not limited to the configuration of the upper ramp surface 28 described above. Additional configurations for the upper ramp surface 28 are conceivable and within the scope of the invention, including, but not limited to, a substantially planar surface parallel to the longitudinal axis.

In accordance with a preferred embodiment of the invention, the implant includes a lower portion 46. The lower portion 46 includes a proximal end 48, a distal end 50, an inner surface 52, and an outer surface 54. The outer surface 54 includes one or more raised ridges 56, for engaging a vertebral endplate of the lower vertebral body. The inner surface 52 defines a lower ramp surface 58.

In accordance with the invention, and as depicted in FIGS. 3 and 15, the lower ramp surface 58 extends from a first position 60 intermediate the proximal end 48 and the distal end 50 to a second position 62 proximate the distal end 14 of the implant 10. A first planar surface 64 extends from the second position 62 to the distal end 14 of the implant 10. The lower ramp surface 58 includes an arcuate portion 66 proximate the second position 62. The arcuate portion 66 intersects with the first planar surface 64 at a second transition point 70. The lower portion 46 further includes, at the proximal end 48, a threaded proximal aperture 44. The invention is not limited to the configuration of the lower ramp surface 58 described above, and depicted in FIGS. 3, 3A and 15. Additional configurations for the lower ramp surface 58 are conceivable and within the scope of the invention, including, but not limited to, a substantially planar surface proximate the first position 60, which ramps upward transverse to the mid-longitudinal axis, defining the ramp surface 58, to the arcuate position 66 proximate the second position 62. The lower ramp surface 58 combines with the upper ramp surface 28 to define an internal pocket 74, internal to the implant 10.

Figure 4:
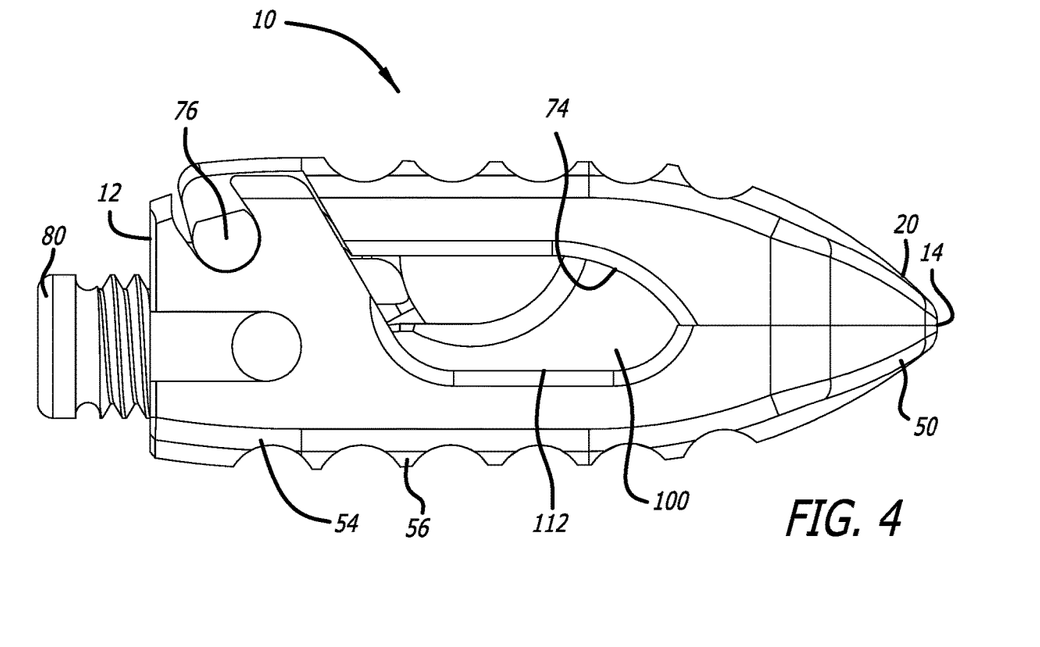
FIG. 4 is a side view of a pivoting wedge expandable spinal implant in accordance with the invention in the collapsed position.

In accordance with a preferred embodiment of the invention, and as depicted in FIG. 4, the upper portion 16 is pivotally connected to the lower portion 46 via a hinge 76 defined at the proximal end 12 of the implant 10.

Figure 5:
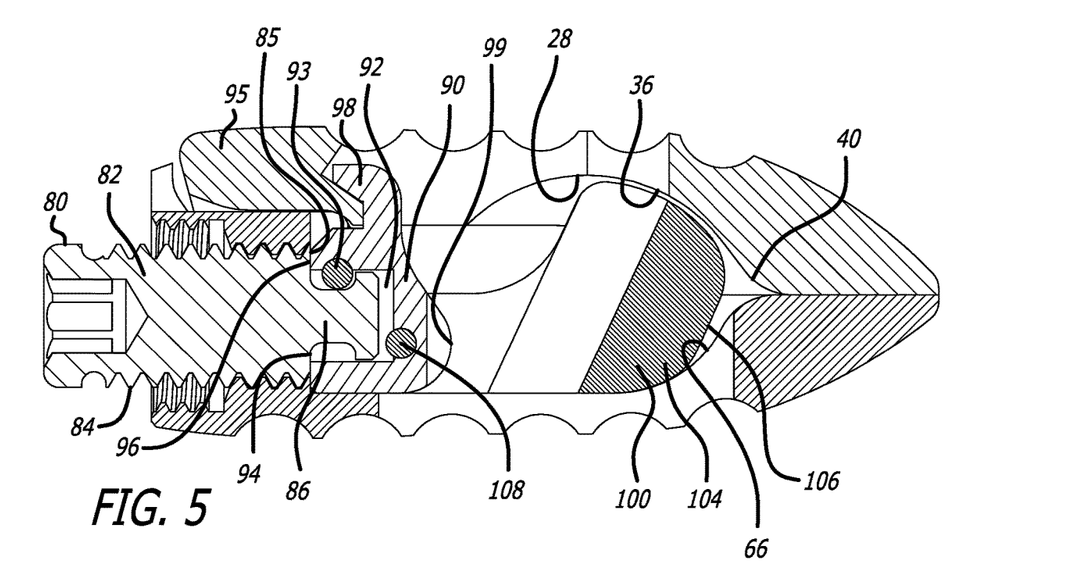
FIG. 5 is a side cross-sectional view of a pivoting wedge expandable spinal implant in accordance with the invention in the collapsed position.

In accordance with a preferred embodiment of the invention, a force application device 80 is provided. As depicted in FIGS. 1-8, force application device 80 is a screw, having a shaft 82. Shaft 82 includes threads 84, a T-shaped distal end 86, and a distal surface 85 that is perpendicular to the mid-longitudinal axis. In the embodiment of FIG. 5, distal surface 85 includes a distal thread. The invention, however, is not limited to use of a screw as the force application device 80, nor is the invention limited to use of a distal thread as the distal surface 85.

In accordance with one embodiment of the invention, a pushing portion 90 is defined in the proximal end 12 of the implant 10. As depicted in FIGS. 5-9, pushing portion 90 includes a proximal end pocket 92. The proximal end pocket 92 includes an opening 94 defined in the proximal end of the proximal end pocket 92. A vertical wall 96 is defined on the pushing portion 90 adjacent the proximal end pocket 92. The pushing portion 90 further includes a hook-shaped projection 98. As depicted in FIG. 5, when the implant 10 is in the collapsed position, the hook-shaped projection 98 engages a locking portion 95 on the upper portion 16 to hold the implant 10 in the collapsed position. As depicted in FIG. 8, however, when the implant 10 is being moved to the expanded position, the force application device is moved through the proximal aperture 44. The hook-shaped projection 98 is pushed away from the locking portion 95 to allow the implant 10 to expand. The T-shaped distal end 86 of the force application device 80 is configured to insert through the opening 94, and move into the proximal end pocket 92 of the pushing portion 90, where it is held in place via a pin 93. The distal surface 85 comes into contact with the vertical wall 96 adjacent the proximal end pocket 92, moving the pushing portion 90 towards the distal end 14 of the implant 10. The motion is then translated by the pushing portion 90, moving the pushing portion 90 toward the distal end 14 of the implant 10.

In accordance with another preferred embodiment of the invention, as depicted in FIG. 8, the pushing portion 90 also includes a distal end pocket 99.

In accordance with a preferred embodiment of the invention, a wedge 100 is provided proximate the distal end 14 of the implant 10. The wedge 100 includes a proximal end 102 and an arcuate distal end 104. The proximal end 102 of the wedge 100 is connected to the pushing portion 90. In one embodiment of the invention, as depicted in FIG. 5, the proximal end 102 of the wedge 100 is attached to the pushing portion 90 with a pin 108. As depicted in FIG. 8, the proximal end 102 of the wedge 100 also can be configured to be engaged to the pushing portion 90 by contact with the distal end pocket 99.

In accordance with another embodiment of the invention, the outer surface 24 of the upper portion 16, and the outer surface 54 of the lower portion 46 are each configured with upper and lower apertures 110, 112, respectively. The upper and lower apertures 110 and 112 provide openings to the internal pocket 74. In addition, the sides of the implant 10 in this embodiment define side apertures 114. In this embodiment of the invention, after the implant 10 is in place in the disc space, bone-growth material packed into the internal pocket 74 of the implant 10 can grow through the respective openings 110, 112, and 114. Suitable bone graft material is well-known in the art. In particular, the side apertures 114 allow the implant 10 to be packed with bone graft material after the implant 10 has been inserted into the disc space.

Figure 9:
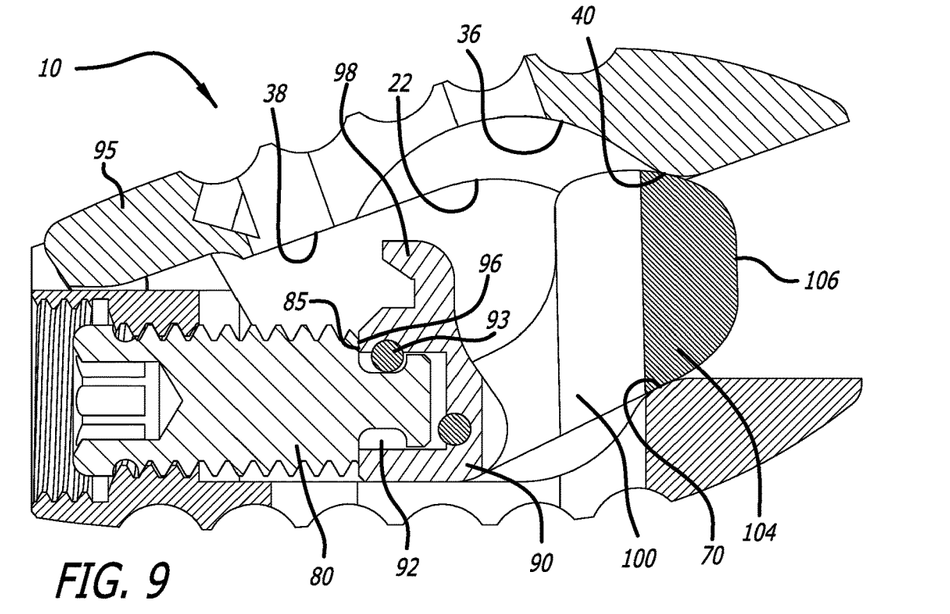
FIG. 9 is a side cross-sectional view a pivoting wedge expandable spinal implant in accordance with the invention expanded to the 100% expanded position.
Figure 11:
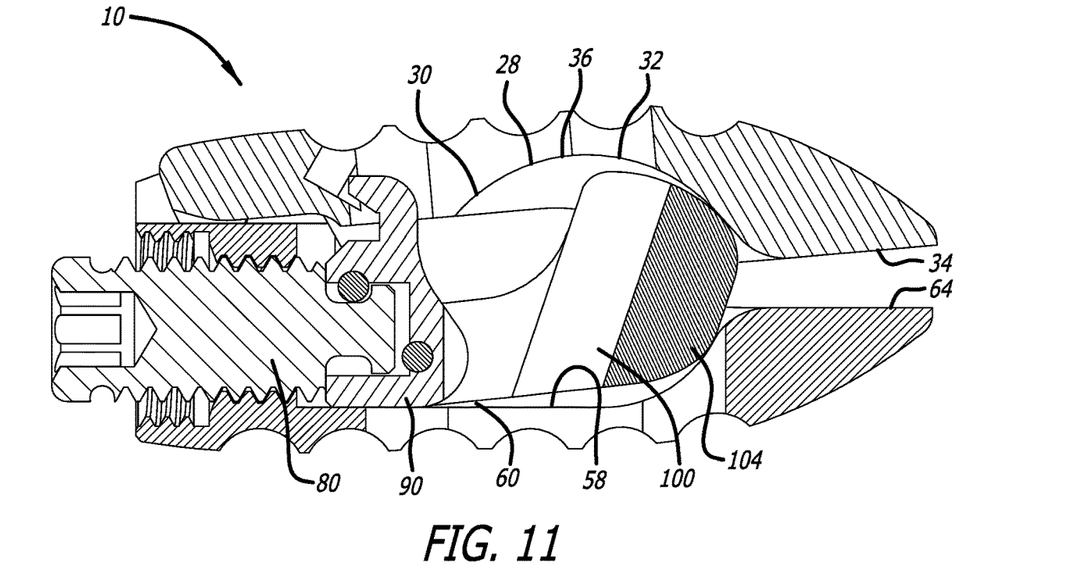
FIG. 11 is a side cross-sectional view of a pivoting wedge expandable spinal implant in accordance with the invention, expanded to the 20% expanded position.
Figure 12:
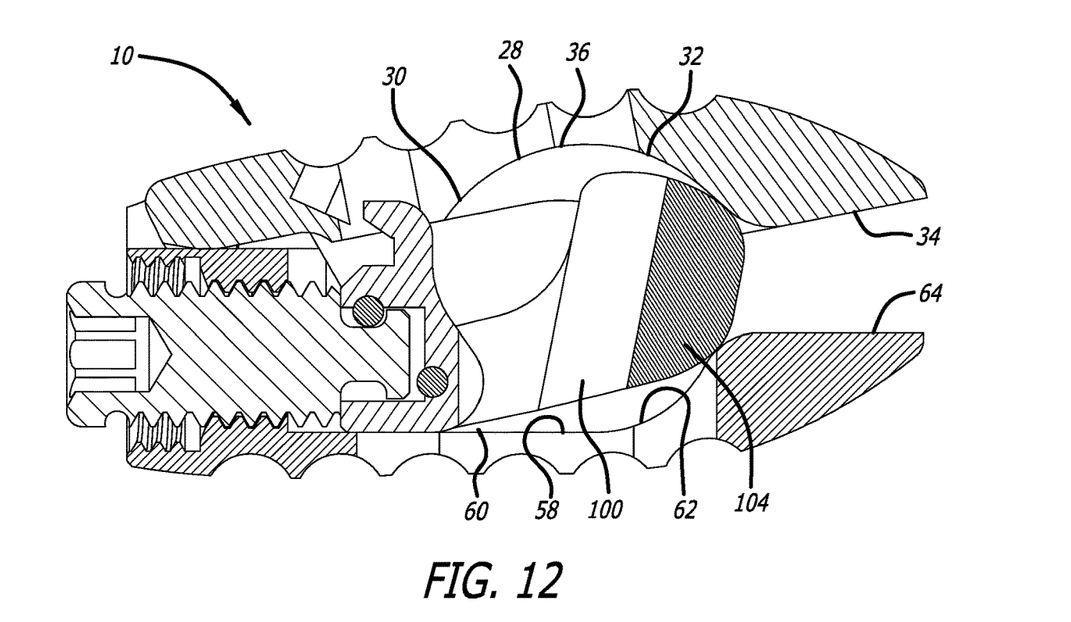
FIG. 12 is a side cross-sectional view of a pivoting wedge expandable spinal implant in accordance with the invention, expanded to the 40% expanded position.
Figure 13:
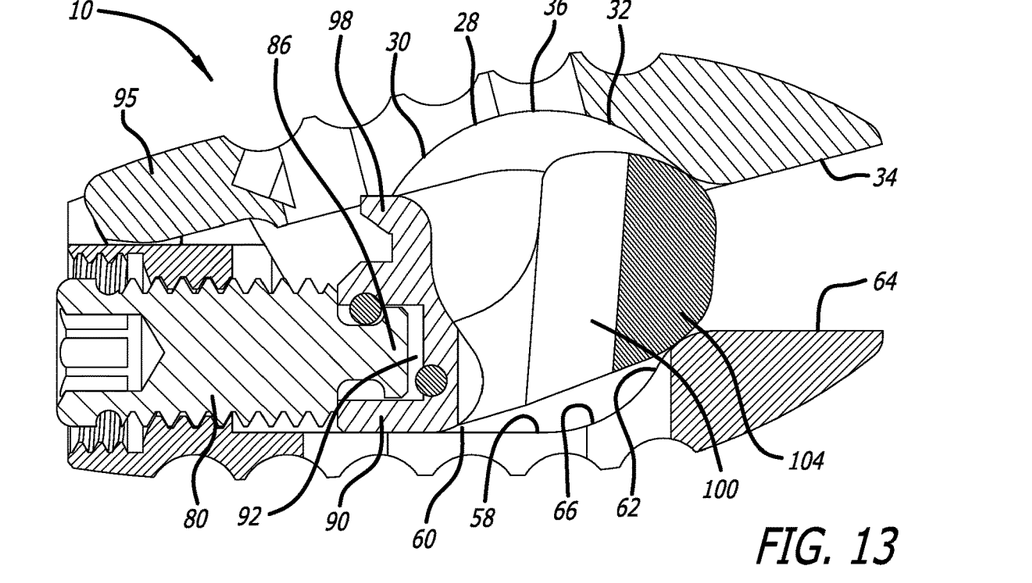
FIG. 13 is a side cross-sectional view of a pivoting wedge expandable spinal implant in accordance with the invention, expanded to the 60% expanded position.
Figure 14:
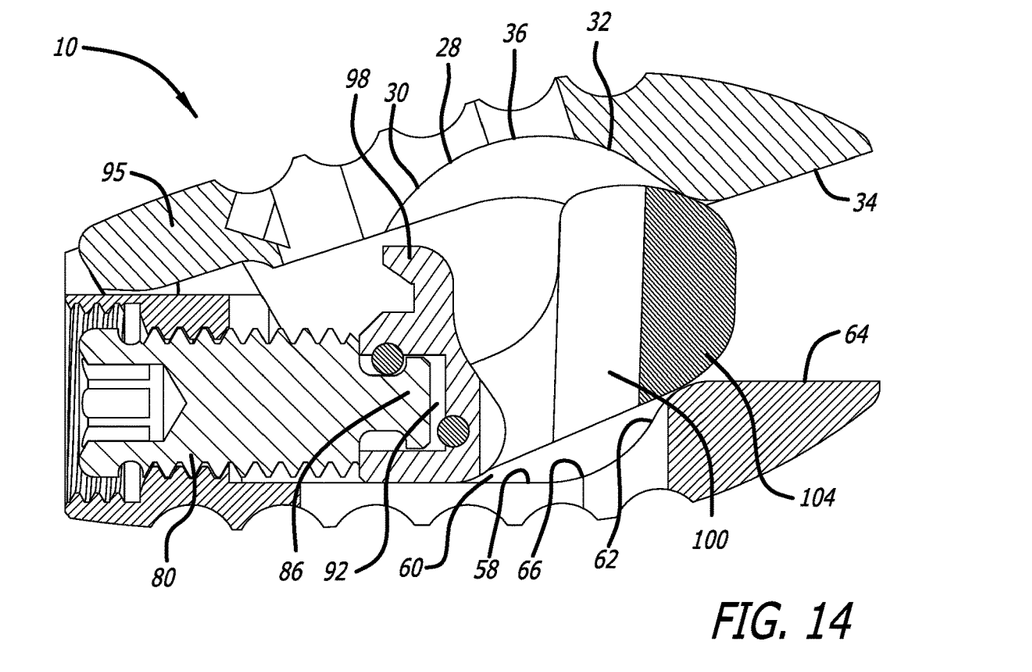
FIG. 14 is a side cross-sectional view of a pivoting wedge expandable spinal implant in accordance with the invention, expanded to the 80% expanded position.

In accordance with a preferred embodiment of the invention, the implant 10 is configured, such that, commencing in the collapsed position, as depicted in FIG. 5, upon translation of the motion from the force application device 80 to the pushing portion 90, subsequent distal motion of the pushing portion 90 is translated to the proximal end 102 of the wedge 100. As depicted in FIG. 11, the arcuate distal end 104 of the wedge 100 moves out of the internal pocket 74, and moves up along the arcuate portion 66 of the lower ramp surface 58 towards the second transition point 70. At this point, as depicted in FIG. 11, the implant 10 is approximately 20% open. As depicted in FIGS. 11 and 12, the wedge 100 moves past the first transition point 40 of the upper ramp surface 28. As depicted in FIG. 12, the implant is approximately 40% open. Subsequently, as depicted in FIGS. 13 and 14, the external radius 106 of the arcuate distal end 104, moves along the internal upper ramp surface 28. In this manner, the force applied to the pushing portion 90 by the force application device 80 is translated into movement of the upper portion 16, thereby pivoting the upper portion 16 on hinge 76, and moving the upper portion 16 away from, the lower portion 46. As depicted in FIG. 13, the implant 10 is approximately 60% open. As depicted in FIG. 14, the implant 10 is approximately 80% open. Movement of the upper portion 16 will continue until the implant 10 achieves the expanded position (i.e., approximately 100% expanded, as depicted in FIG. 9).

Figure 10:
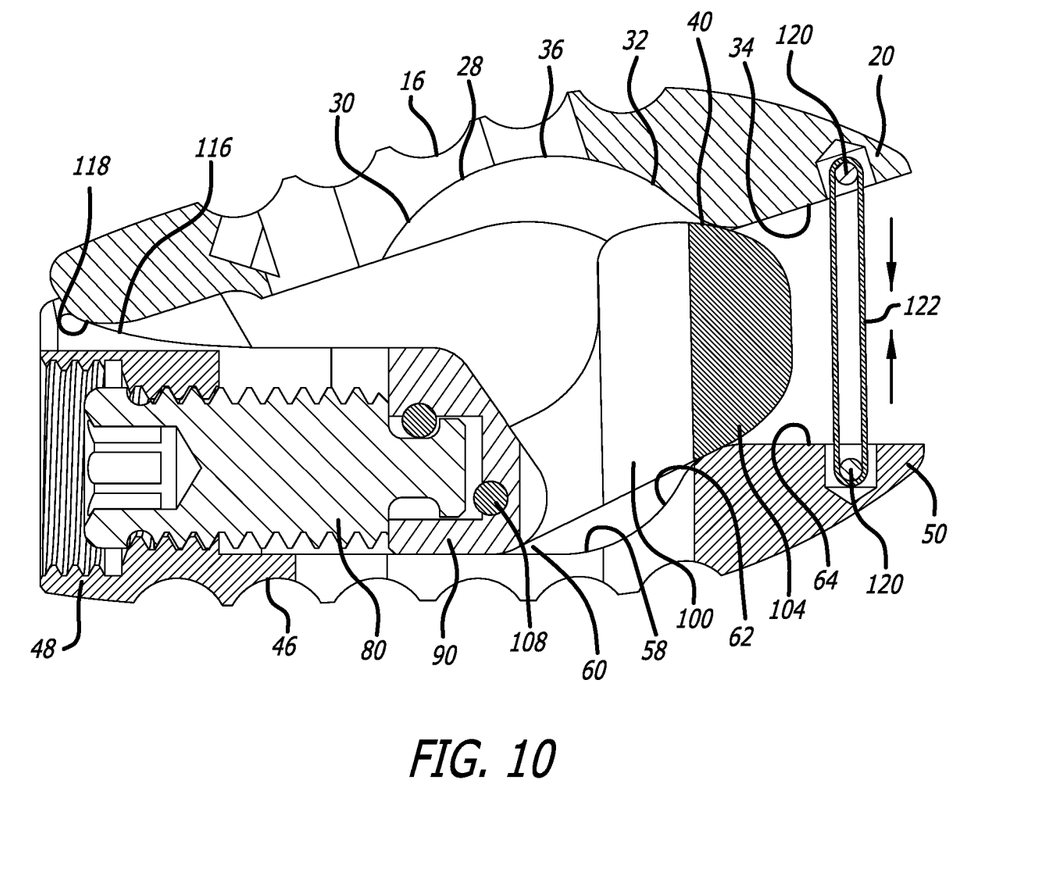
FIG. 10 is a side cross-sectional view of a pivoting wedge expandable spinal implant in accordance with another embodiment of the invention.

In accordance with another embodiment of the invention, as depicted in FIG. 10, the implant 10 may include an arcuate posterior ramp portion 116 defined on the pushing portion 90. As depicted in FIG. 10, the proximal end 18 of the upper portion 16 includes an arcuate portion 118. The arcuate posterior ramp portion 116 has a radius which is larger than a radius of the arcuate posterior ramp portion 118. Alternatively, the posterior ramp portions may have straight inclines, or multiple curves. Interaction between these two arcuate components further moves the upper portion 16 of the implant 10 away from the lower portion 46 of the implant 10.

In accordance with another embodiment of the invention, as depicted in FIG. 10, the distal end 14 of the implant 10 may include distal end projecting pins 120 projecting from the upper portion 16 and the lower portion 46. An elastic member 122 may be wrapped around the distal end projecting pins 120. Upon translation of the force application device from the distal end of the implant, the elastic member 122 assists pulling the upper portion 16 and the lower portion 46 back together in the collapsed position.

In accordance with a preferred embodiment of the invention, a disc space of a patient between an upper vertebral body and a lower vertebral body is surgically prepared. An implant 10, having the configuration of the invention as described above, is inserted into the disc space, either via a posterior approach, or via a lateral approach. The implant 10 is inserted into the disc space in the collapsed position. The ridges 26 on the outer surface 24 of the upper portion 16 engage a vertebral endplate of the upper vertebral body. Likewise, the ridges 56 on the outer surface 54 of the lower portion 46 engage a vertebral endplate of the lower vertebral body. As depicted in FIG. 5, the hook-shaped projection 98 on the pushing portion 90 is engaged with the locking portion 95 of the upper portion 16, assisting in holding the upper portion 16 in place over the lower portion 46, assisting in keeping the implant 10 in the collapsed position.

In accordance with a preferred embodiment of the invention, the force application device 80, preferably in the form of a threaded screw, is moved in the threaded proximal aperture 44 toward the distal end 20 of the implant 10. The T-shaped distal end 86 is held in place in the proximal end pocket 92 by the pin 93. The distal surface 85 contacts the vertical wall 96 adjacent the proximal end pocket 92, translating motion of the force application device 80 to the pushing portion 90. The pushing portion 90 moves toward the distal end 14 of the implant 10. This motion causes the hook-shaped projection 98 to be disengaged from the locking portion 95 on the upper portion 16.

Figure 6:
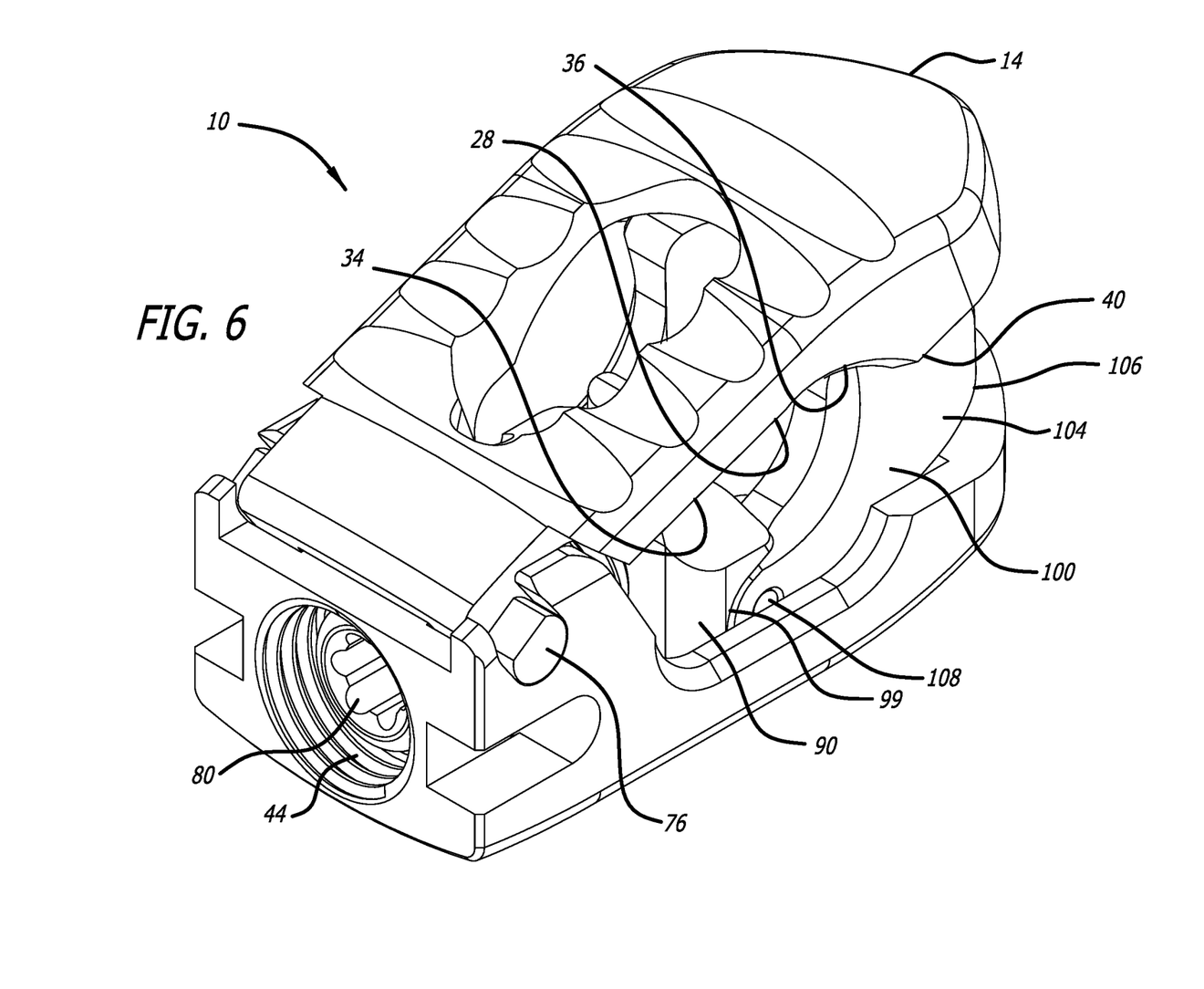
FIG. 6 is a lower perspective view of a pivoting wedge expandable spinal implant in accordance with the invention in the process of expanding to the expanded position.
Figure 7:
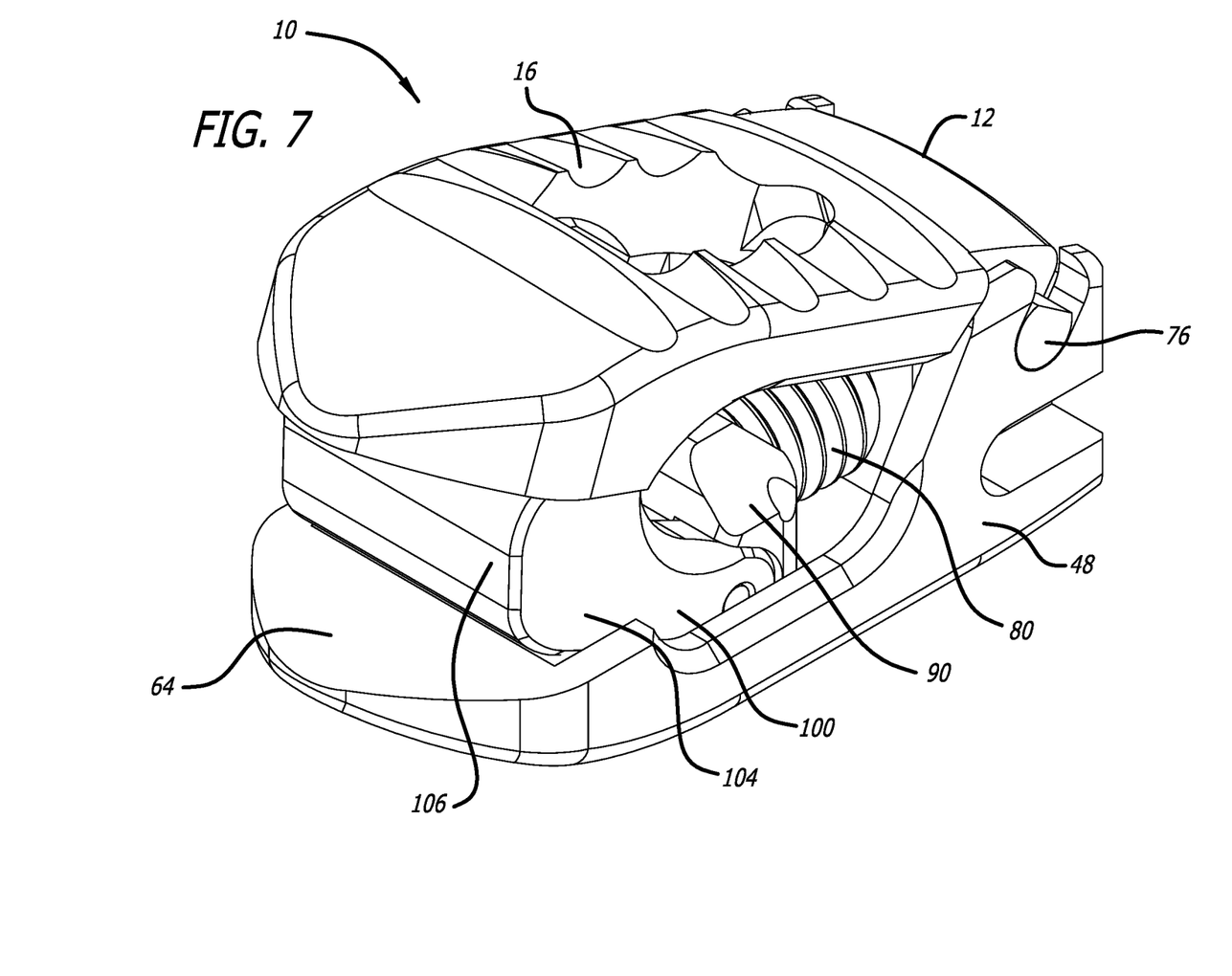
FIG. 7 is an upper perspective view of a pivoting wedge expandable spinal implant in accordance with the invention in the process of expanding to the expanded position.
Figure 8:
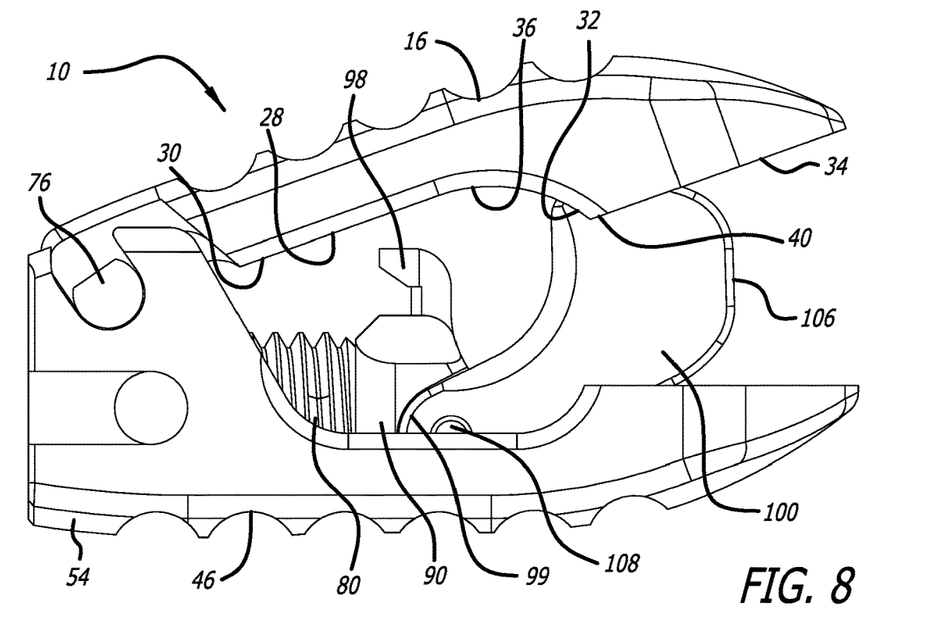
FIG. 8 is a side view of a pivoting wedge expandable spinal implant in accordance with the invention in the process of expanding to the expanded position.

In accordance with a preferred embodiment of the invention, and as depicted in FIGS. 5-7, the motion of the pushing portion 90 is subsequently translated to the proximal end 12 of the wedge 100. The wedge 100 moves toward the distal end 14 of the implant 10, while the pin 108 may or may not remain unloaded. The arcuate distal end 104 of the wedge 100 is pushed out of the internal pocket 74, and up the lower ramp surface 58, past the second transition point 70, and into contact with the first transition point 40 on the upper portion 16. Motion translated to the upper portion 16, causes the upper portion 16 to rotate upward on hinge 76, away from lower portion 46.

In accordance with a preferred embodiment of the invention, as the upper portion 16 commences to move the arcuate distal end 104 of the wedge 100 moves along the upper ramp surface 28, moving the upper portion away from the lower portion. The arcuate distal end 104 of the wedge 100 continues to move up the upper ramp surface 28 until the implant 10 has reached the expanded position.

In accordance with the invention, in the process of being expanded from the collapsed position to the expanded position, the wedge 100 both pivots and engages two ramps, while the pin 108 may or may not remain unloaded. The internal pocket 74 between the upper ramp surface 28 and the lower ramp surface 58 carries the majority of all of the force between the pushing portion 90 and the components of the wedge 100. The resulting degree of expansion in the expanded position of the implant 10 is significantly increased when compared to a non-pivoting wedge. The increased degree of expansion of the implant 10 in the expended position results in an increased angle between the lower portion 46 and the upper portion 16. This increased angle results in increased lordosis between the upper and lower vertebral bodies.

Figure 17:
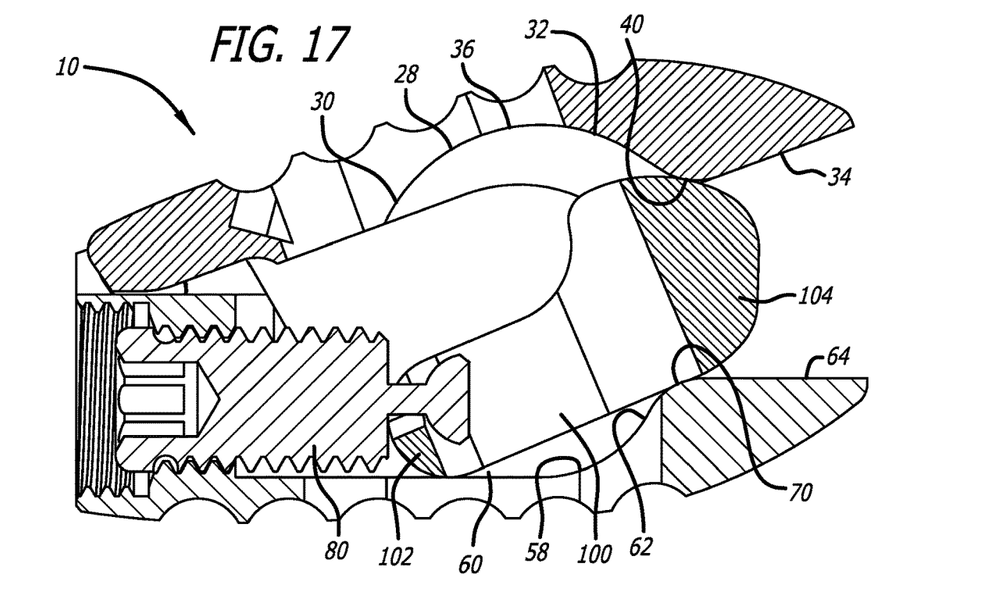
FIG. 17 is a lower perspective cross-sectional view of the pivoting wedge expandable spinal implant depicted in FIG. 15, expanded to a 40% expanded position.
Figure 18:
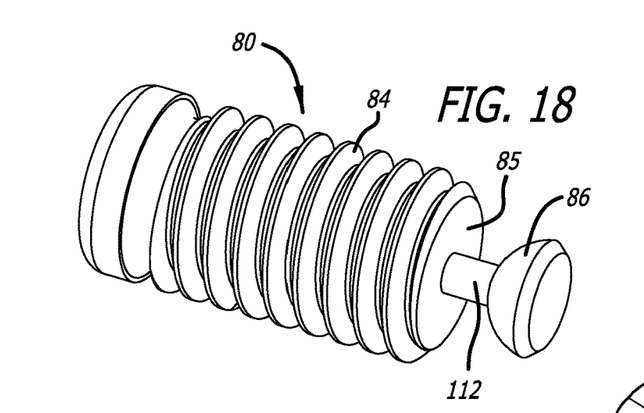
FIG. 18 is an upper perspective view of a threaded force application device, used in the pivotal wedge expandable spinal implant depicted in FIG. 15.
Figure 19:
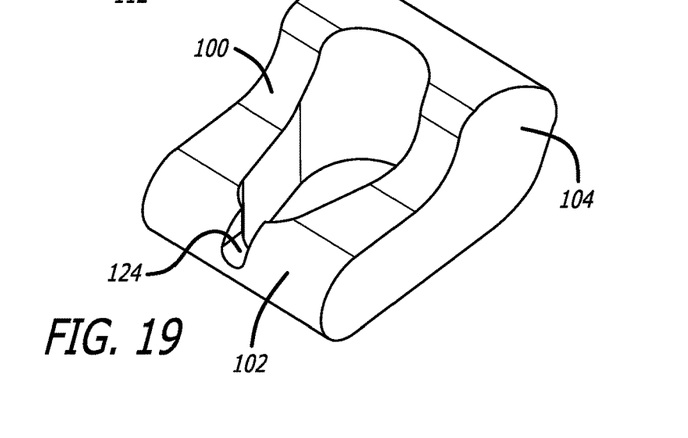
FIG. 19 is an upper perspective view of a wedge, used in the pivotal wedge expandable spinal implant depicted in FIG. 15.

In accordance with another preferred embodiment of the invention, as depicted in FIGS. 17-19, the implant 10 does not include a pushing portion 90. In this embodiment, a stem 112 of the T-shaped distal end 86 of the force application device 80 fits into a notch 124 defined in the proximal end 102 of the wedge 100. With this configuration the force application device 80 is positioned to translate motion directly to the proximal end 102 of the wedge 100. Rotation of the threaded force application device 80 in the threaded proximal aperture 44 moves the force application device 80 toward the distal end 14 of the implant 10. Contact between the distal surface 85 of the force application device 80 with the distal end 102 of the wedge 100 translates the motion of the force application device 80 directly to the wedge 100, thereby moving the wedge 100 toward the distal end 14 of the implant 10. The wedge 100 is moved along the lower ramp surface 58 into contact with the upper ramp surface 28. The wedge 100 moves along the upper ramp surface 28, rotating the upper ramp surface 28, on the hinge 76, away from the lower ramp surface 58, until the implant 10 reaches the expanded position.

Other embodiments of the invention will be apparent to those skilled in the art from consideration of the specification and practice of the invention disclosed herein. For example, and not by way of limitation, a modular upper portion 16 can be removed, e.g., by disconnecting the modular upper portion 16 from the lower portion 46 at the hinge 76, and replacing the removed modular upper portion with another modular upper portion 16, which may have different dimensions. In addition, all of the components described above as being associated with the upper portion, and all of the components described above as being associated with the lower portion can be switched, i.e., the upper and lower portions can be entirely reversed in orientation, and the resultant implant would still fall within the spirit and scope of the present invention. The specification and examples are to be considered as exemplary only, with a true scope and spirit of the invention being indicated by the following claims.

We claim:

1. An expandable spinal implant for insertion into a patient's disc space between an upper vertebral body and a lower vertebral body, the implant comprising:

a proximal end, an opposite distal end, a length extending between the proximal end and the distal end, and a mid-longitudinal axis extending through the proximal end and the distal end;

an upper portion extending between the proximal end and the distal end of the expandable spinal implant, the upper portion having an upper inner surface;

a lower portion extending between the proximal end and the distal end of the expandable spinal implant, the lower portion being pivotally engaged with the upper portion, and having a lower inner surface, the lower inner surface including a ramp portion proximate the distal end of the expandable spinal implant, the ramp portion extending upwardly toward the upper portion in a direction transverse to the mid-longitudinal axis;

a force application device, at least a portion of the force application device being moveable relative to at least the proximal end of the expandable spinal implant, the force application device including at least a distal surface, and being configured to alternately move the distal surface toward or away from the distal end of the implant via actuation thereof; and a moveable portion positioned between the upper portion and the lower portion, and having a proximal end portion and a distal end portion pivotally attached to one another, the proximal end portion being positioned to contact the distal surface of the force application device, and the distal end portion being configured for contact with the upper portion and for slidable movement along the lower inner surface and the ramp portion between a first position proximate the proximal end and a second position proximate the distal end, wherein movement of the force application device causes corresponding slidable movement of at least a portion of the distal end portion along the lower inner surface and the ramp portion, wherein the ramp portion forces the portion of the distal end portion upwardly relative to the proximal end portion to contact the upper portion, and wherein contact of the proximal end portion with the upper portion via movement of the portion of the distal end portion along the ramp portion moves the upper portion and the lower portion apart from one another from a collapsed position to an expanded position.

2. The expandable spinal implant of claim 1, wherein the upper portion includes a first outer surface that is configured to engage a vertebral endplate of the upper vertebral body, and the lower portion includes a second outer surface that is configured to engage a vertebral endplate of the lower vertebral body.

3. The expandable spinal implant of claim 2, wherein at least one of the first outer surface and the second outer surface includes an aperture defined therein to allow bone growth therethrough.

4. The expandable spinal implant of claim 1, wherein the force application device comprises a threaded screw.

5. The expandable spinal implant of claim 1, wherein a distal end surface of the distal end portion is substantially arcuate, the arcuate distal end surface being configured to contact portions of the lower inner surface and the upper inner surface.

6. The expandable spinal implant of claim 1, wherein the distal end of the implant further comprises a collapsed position return structure, the collapsed position return structure being configured to pull the upper portion and the lower portion at the distal end in the direction of the collapsed position upon retraction of the force application device.

7. The expandable implant of claim 1, further comprising a hook-shaped projection positioned proximate the force application device, the hook-shaped projection being engageable with a locking portion positioned on the upper portion, to at least temporarily hold the implant in the collapsed position.

8. The expandable implant of claim 1, wherein the lower portion includes an opening defined in the proximal end, the opening including an inner peripheral surface, the inner peripheral surface including at least one thread defined thereon.

9. The expandable implant of claim 8, wherein the force application device includes an elongated shaft, the elongated shaft including an outer peripheral surface, the outer peripheral surface including at least one thread defined thereon, the at least one thread on the outer peripheral surface of the shaft being configured to engage the at least one thread on the inner peripheral surface of the opening.

10. The expandable implant of claim 1, further comprising a pin for pinning the proximal end portion and the distal end portion to one another to facilitate pivotal attachment thereof.

11. An expandable spinal implant for insertion into a patient's disc space between an upper vertebral body and a lower vertebral body, the implant comprising:
    a proximal end, an opposite distal end, a length extending between the proximal end and the distal end, and a mid-longitudinal axis extending through the proximal end and the distal end;
    an upper portion extending between the proximal end and the distal end of the expandable spinal implant, the upper portion having an upper inner surface;
    a lower portion extending between the proximal end and the distal end of the expandable spinal implant, the lower portion being pivotally engaged with the upper portion, and having a lower inner surface, the lower inner surface including a ramp portion proximate the distal end;
    a force application device having a distal end surface and being alternately moveable toward or away from the distal end of the implant via actuation of the force application device; and
    a moveable portion positioned between the upper portion and the lower portion, and having a proximal end portion and a distal end portion pivotally attached to one another, the proximal end portion being positioned to contact the distal end surface of the force application device, and the distal end portion being configured for slidable movement along the lower surface and the ramp portion and contact with the upper portion,
    wherein movement of the force application device causes corresponding slidable movement of at least a portion of the distal end portion along the lower inner surface and the ramp portion, wherein the ramp portion forces the portion of the distal end portion upwardly relative to the proximal end portion to contact the upper portion, and wherein the ramp portion directs the portion of the distal end portion upwardly to contact the upper portion to move the upper portion away from the lower portion, and move the implant from a collapsed position to an expanded position.

12. The expandable spinal implant of claim 11, wherein the upper portion includes a first outer surface and the lower portion includes a second outer surface, and at least one of the first outer surface of the upper portion and the second outer surface of the lower portion includes an aperture defined therein to allow bone growth therethrough.

13. The expandable spinal implant of claim 11, wherein a distal end surface of the distal portion is substantially arcuate, the arcuate distal end surface being configured to contact portions of the lower inner surface and the upper inner surface.

14. The expandable implant of claim 11, further comprising a hook-shaped projection positioned proximate the force application device, the hook-shaped projection being engageable with a locking portion positioned on the upper portion, to at least temporarily hold the implant in the collapsed position.

15. The expandable implant of claim 11, wherein the lower portion includes an opening defined in the proximal end, the opening including an inner peripheral surface, the inner peripheral surface including at least one thread defined thereon.

16. The expandable implant of claim 15, wherein the force application device includes an elongated shaft, the elongated shaft including an outer peripheral surface, the outer peripheral surface including at least one thread defined thereon, the at least one thread on the outer peripheral surface of the shaft being configured to engage the at least one thread on the inner peripheral surface of the opening.

17. The expandable implant of claim 11, further comprising a pin for pinning the proximal end portion and the distal end portion to one another to facilitate pivotal attachment thereof.

18. An expandable spinal implant for insertion into a patient's disc space between an upper vertebral body and a lower vertebral body, the implant comprising:
    a proximal end, an opposite distal end, a length extending between the proximal end and the distal end, and a mid-longitudinal axis extending through the proximal end and the distal end;
    an upper portion having an upper inner surface;
    a lower portion being pivotally engaged with the upper portion, and having a lower inner surface, the lower inner surface including a ramp portion proximate the distal end of the expandable spinal implant, the lower surface and the upper surface defining an internal cavity therebetween;
    a force application device, at least a portion of the force application device being moveable relative to at least the proximal end of the expandable spinal implant, the force application device including at least a distal surface, and being configured to alternately move the distal surface toward or away from the distal end of the implant via actuation thereof;
    a moveable portion positioned in the internal cavity, and having a proximal end portion and a distal end portion pivotally attached to one another, the proximal end portion being positioned to contact the distal surface of the force application device, and the distal end portion being configured for slidable movement along the lower surface and the ramp portion between a first position and a second position, wherein movement of the force application device causes corresponding slidable movement of at least a portion of the proximal end portion along the lower surface and the ramp portion, the ramp portion forcing the portion of the distal end portion pivot upwardly with respect to the proximal end portion to contact the upper portion to move the upper portion and the lower portion apart from one another.

19. The expandable implant of claim 18, wherein the lower portion includes an opening defined in the proximal end, the opening including an inner peripheral surface, the inner peripheral surface including at least one thread defined thereon, and wherein the force application device includes an elongated shaft, the elongated shaft including an outer peripheral surface, the outer peripheral surface including at least one thread defined thereon, the at least one thread on the outer peripheral surface of the shaft being configured to engage the at least one thread on the inner peripheral surface of the opening.

20. The expandable implant of claim 18, further comprising a hook-shaped projection positioned proximate the force application device, the hook-shaped projection being engageable with a locking portion positioned on the upper portion, to at least temporarily hold the implant in the collapsed position.

* * * * *